United States Patent [19]

Jacobson

[11] Patent Number: 5,728,887
[45] Date of Patent: Mar. 17, 1998

[54] CATALYTIC HYDROGENOLYSIS OF ORGANIC THIOCYANATES AND DISULFIDES TO THIOLS

[75] Inventor: Stephen Ernest Jacobson, Princeton Junction, N.J.

[73] Assignee: E. I. du Pont de Nemours and Company, Wilmington, Del.

[21] Appl. No.: 629,824

[22] Filed: Apr. 10, 1996

[51] Int. Cl.$^6$ .................................................. C07C 319/00
[52] U.S. Cl. ............................. 568/65; 568/68; 568/69
[58] Field of Search .............................. 568/65, 67, 68, 568/69

[56] References Cited

U.S. PATENT DOCUMENTS

| | | | |
|---|---|---|---|
| 3,940,435 | 2/1976 | Hiestand | 260/481 R |
| 4,958,039 | 9/1990 | Pechhold | 556/421 |
| 5,202,443 | 4/1993 | Schneider et al. | 548/533 |
| 5,411,766 | 5/1995 | Kirchner | 427/393.4 |
| 5,449,655 | 9/1995 | Albers | 502/185 |
| 5,493,058 | 2/1996 | Cadot et al. | 568/70 |

FOREIGN PATENT DOCUMENTS

| | | | |
|---|---|---|---|
| 9184 611 | 3/1992 | Australia . | |
| 1 242 219 | 9/1988 | Canada | 260/625.5 |
| 0 134 200 A1 | 3/1985 | European Pat. Off. . | |
| 649 837 A1 | 4/1995 | European Pat. Off. | C07C 319/06 |
| 208526 | 11/1993 | Hungary . | |
| 1205537 | 9/1970 | United Kingdom | C07C 149/28 |

OTHER PUBLICATIONS

Victor L. Mylroie and Joseph K. Doles, Reduction of Sulfonyl Chlorides to Thiols, *Catalysis of Organic Reactions*, D.W. Blackburn, Ed. Marcel Dekker Inc., New York, New York, pp. 189–196, 1990.

*Primary Examiner*—Samuel Barts

[57] ABSTRACT

A process for the preparation of a thiol comprising reacting hydrogen with a thiocyanate or disulfide wherein the reaction with thiocyanate is conducted in the presence of a catalyst comprising a Group VIII metal or a mixture thereof; and the reaction with thiocyanate or with disulfide is conducted in the presence of a catalyst comprising a Group VIII metal or mixture thereof in the presence of a modifier metal selected from a group consisting of Group IB, Group IIB, Group IIIA, Group IVA, Group VA and Group VIA metal or mixture thereof, said catalyst being on a porous insoluble support.

9 Claims, No Drawings

CATALYTIC HYDROGENOLYSIS OF ORGANIC THIOCYANATES AND DISULFIDES TO THIOLS

FIELD OF THE INVENTION

This invention relates to a process for the catalytic hydrogenolysis of organic thiocyanates and disulfides to produce thiols.

BACKGROUND OF THE INVENTION

Conventional processes for organic thiol synthesis use hydrides such as lithium aluminum hydride or Zn-HCl as reducing agents to convert organic thiocyanates or sulfides to thiols. A common industrial method for thiol synthesis involves reaction of an alkyl halide with thiourea to give an isothiuronium salt, which is cleaved with alkali or high molecular weight amine to give the thiol. Thiourea is a carcinogen with exposure hazards and requires special equipment and expense, such as incinerators, for safety.

The process described in U.S. Pat. No. 5,202,443, which is the final step in the preparation of a therapeutic compound, converts a thiocyanate derivative to the corresponding thiol by hydrogenolysis using a palladium on charcoal catalyst. A modifier metal is not used. Relatively low yields are obtained, even at high levels of catalyst usage.

There is a need for an economical and environmentally acceptable process for the production of organic thiols in high yield from thiocyanates and disulfides. The process of the present invention fulfills this need.

SUMMARY OF THE INVENTION

The present invention comprises a process for the preparation of thiols of formula I or II $$R_1-(X)_a-SH, \text{ or} \quad \quad I$$

    II wherein

X is $(CH_2)_m$ wherein m is 1 or 2;

a is zero or 1;

$R_1$ is:

$C_1-C_{30}$ linear, branched, or cyclic alkyl optionally substituted with a $C_1-C_{30}$ perfluroralkyl;

$C_1-C_{30}$ perfluoroalkyl;

H—D—G or F—E—G wherein

D is —$(CH_2)_b$—;

E is —$(CF_2)_b$—;

G is —[A—$(CH_2)_c]_d$—$(CH_2)_e$—, —[A—$(CF_2)_c]_d$—$(CF_2)_e$—, —[A—$(CF_2)_c]_d$—$(CH_2)_e$—, or —[A—$(CH_2)_c]_d$—$(CF_2)_e$—;

wherein each A is independently selected from the group consisting of —$N(R_3)$—, —$C(O)N(R_3)$—, —$CO_2$—, —$SO_2N(R_3)$—, —O—, and —S—; wherein $R_3$ is H, $C_1-C_{30}$ alkyl, or $C_1-C_{30}$ perfluroralkyl; each b and e is independently zero or a positive integer of 1 to 29, and each c and d is independently a positive integer of 1 to 30, provided that b+e+(c×d) is less than or equal to 30; and $C_6-C_{30}$ aryl optionally substituted with $C_1-C_{24}$ alkyl, C1-C24 perfluoroalkyl, F, Br, Cl $N(R_3)_2$, $CON(R_3)_2$, $CO_2(R_3)$, $CO(R_3)$, $SO_2N(R_3)_2$, $O(R_3)$, or $S(R_3)$ wherein $R_3$ is H, $C_1-C_{30}$ alkyl, or $C_1-C_{30}$ perfluoroalkyl; and $R_2$ is —D—G— or —E—G— wherein D, E and G are as defined above provided that b+e+(c×d) is less than or equal to 8;

said process comprising reacting hydrogen with,

A. a thiocyanate of formula III $$R-(X)_a-SCN \quad \quad III$$

wherein R is $R_1$ or $R_2$ as defined above and X and a are as defined above for formula I and II, in the presence of a catalyst comprising a Group VIII metal or mixture thereof, or said metal in the presence of a modifier metal selected from the group consisting of a Group IB, Group IIB, Group IIIA, Group IVA, Group VA and Group VIA metal, or mixture thereof, said catalyst being on a porous insoluble support.

The present invention further comprises the preparation of a thiol of formula I or II as defined above comprising reacting hydrogen with a disulfide of Formula IV $$R-(X)_a-S-S-(X)_a-R \quad \quad IV$$

wherein R is $R_1$ or $R_2$ as defined above and X and a are as defined above for Formula I and II, in the presence of a catalyst comprising a Group VIII metal or mixture thereof in the presence of a modifier metal selected from a group consisting of Group IB, Group IIB, Group IIIA, Group IVA, Group VA, and Group VIA metal, or mixture thereof, said catalyst being on a porous insoluble support.

DETAILED DESCRIPTION OF THE INVENTION

The process of the present invention is useful for the hydrogenolysis of many organic thiocyanates and disulfides. Suitable thiocyanates and disulfides for use as reactants herein include those of Formula III and IV respectively, $$R-(X)_a-SCN \quad \quad III$$

$$R-(X)_a-S-S-(X)_a-R \quad \quad IV$$

wherein X is $(CH_2)_m$ wherein m is 1 or 2, a is zero or 1, and R is an organic radical as defined above for $R_1$ and $R_2$. For example R is $R_1$ and is an alkyl radical of 1 to about 30 carbons, including linear, branched or cyclic structures, such as methyl, ethyl, propyl, butyl, isopropyl, isobutyl, sec-butyl, tert-butyl, cyclopropyl, or cyclobutyl. R is also a perfluoroalkyl group of 1 to about 30 carbons such as perfluorobutyl, perfluorobutylethyl, or perfluorohexylethyl. Such compounds are available as fluorotelomer intermediates from E. I. du Pont de Nemours and Company, Wilmington, Del. as "ZONYL" Fluorochemical Intermediates.

R is also H—D—G or F—E—G wherein D is —$(CH_2)_b$—; E is —$(CF_2)_b$—; and G is —[A—$(CH_2)_c]_d$—$(CH_2)_e$—, —[A—$(CF_2)_c]_d$—$(CF_2)_e$—, —[A—$(CF_2)_c]_d$—$(CH_2)_e$—, or —[A—$(CH_2)_c]_d$—$(CF_2)_e$—. Each A is independently selected from —$N(R_3)$—, —$C(O)N(R_3)$—, —$CO_2$—, —$SO_2N(R_3)$—, —O—, and —S — wherein $R_3$ is H, C, $C_1-C_{30}$ alkyl, or $C_1-C_{30}$ perfluoroalkyl; each b and c is independently zero or a positive integer of 1 to 29, and each c and d is independently a positive integer of 1 to 30, provided that b+e+(c×d) is less than or equal to 30.

Therefore R includes the following:

1) $H(CH_2)_b$—[A—$(CH_2)_c]_d$—$(CH_2)_e$—
2) $F(CF_2)_b$—[A—$(CF_2)_c]_d$—$(CF_2)_e$—
3) $H(CH_2)_b$—[A—$(CF_2)_c]_d$—$(CF_2)_e$—
4) $F(CF_2)_b$—[A—$(CH_2)_c]_d$—$(CH_2)_e$—
5) $H(CH_2)_b$—[A—$(CF_2)_c]_d$—$(CH_2)_e$—
6) $H(CH_2)_b$—[A—$(CH_2)_c]_d$—$(CF_2)_e$—

7) $F(CF_2)_b$—[A—$(CH_2)_c]_d$—$(CF_2)_e$—
8) $F(CF_2)_b$—[A—$(CF_2)_c]_d$—$(CH_2)_e$—

In addition R is an aryl radical of 6 to about 30 carbons comprising phenyl, naphthyl, biphenyl, and the like, or a substituted aryl radical. Typical substituents are an alkyl group of 1 to about 24 carbons such as methyl, ethyl, propyl, butyl, isopropyl, isobutyl, sec butyl, tert butyl, cyclopropyl, cyclobutyl, and the like; perfluoroalkyl group or of 1 to about 24 carbons such as perfluorobutyl, perfluorobutylmethyl, perfluorohexylmethyl, perfluorobutylethyl, or perfluorophenylethyl; $N(R_2)$; $C(O)N(R_2)$; $CO_2(R_3)$; $CO(R_3)$; F; Cl; Br; $SO_2N(R_3)_2$; $O(R_2)$; and $S(R_3)$ wherein $R_3$ is H, $C_1$-$C_{20}$ alkyl, or $C_1$-$C_{30}$ perfluoroalkyl When R is $R_2$ and divalent, it is —D—G— or —E—G— wherein D, E, and G are defined above. In this case b+e+(c×d) is less than or equal to 8. R can be represented as the above formulae numbered 1 to 16 wherein the initial F or H is replaced by a bond. The two terminal bonds connect to CH—(X)a-SH in formula II thereby forming a ring structure with the initial carbon atom.

Preferred as reactants herein are Telomer B thiocyanate and Telomer B disulfide. These reactants are examples of Formula III and IV wherein a is one. The term "Telomer B thiocyanate" is used herein to mean $F(CF_2)_x(CH_2)_y$— SCN wherein x is 4 to 20 and y is 2, or mixtures thereof. The term "Telomer B disulfide" is used herein to mean $F(CF_2)_x(CH_2)_y$—S—S—$(CH_2)_x(CF_2)_y$F wherein x is 4 to 20 and y is 2, or mixtures thereof.

Preferred is wherein x is 6, 8, 10 or 12 as in perfluorohexyl, perfluorooctyl, perfluorodecyl, and perfluorododecyl.

Preferred carbon chain length distributions for x in Telomer B thiocyanate and Telomer B disulfide, when they occur as mixtures, are as follows:

1) $C_4$-6%, $C_6$-56%, $C_8$-26%, $C_{10}$-8%, and $C_{12}$-4%;
2) $C_4$-0.2%, $C_6$-33%, $C_8$-35%, $C_{10}$-19%, and $C_{12}$-12.8%;
3) $C_4$-0.2%, $C_6$-2%, $C_8$-54%, $C_{10}$-30%, $C_{12}$-10%, $C_{14}$-3%, and $C_{16}$-0.8%.

The process of the present invention typically provides very high yields (98–100 wt %). For example the thiol 2-perfluorohexyl-1-ethanethiol generated by hydrogenolysis of fluorotelomer intermediates such as 2-perfluorohexylethanethiocyanate or bis-(2-perfluorohexylethane)-disulfide is obtained at a 98–100 wt % yield.

Catalysts used in the process of the present invention comprise a Group VIII metal or mixture of Group VIII metals for the hydrogenolysis of thiocyanates. A Group VIII metal or mixture thereof plus a modifier metal selected from the group consisting of Group IB, Group IIB, Group IIIA, Group IVA, Group VA and Group VIA, or a mixture thereof, is used for the hydrogenolysis of thiocyanate or disulfide. The catalyst is supported on a porous inert material which is insoluble in solvents which may be used in the process. The preferred catalytic metals are Pd, Pt and Ru and the preferred modifier metals are Cu, Ag, Au, Sn, Pb, Bi, In, Tl, S, Se and Te. Materials useful as supports include, activated carbon, alumina, silica, alumino-silicates, zirconia, titania, calcium carbonate, zeolites, and magnesia.

When a modifier metal is present, the catalyst comprises from about 1% to about 20% by weight of Group VIII metal and from about 0.1% to about 5% by weight of modifier metal, the balance being the support component. When a modifier is not present the catalyst comprises from about 1% to about 20% by weight of Group VIII metal, the remainder being the support component. A preferred composition is 1–20 wt % Pd and 0.1 to 1 wt % Sn on activated carbon. It is also preferred that the Group VIII metal be prereduced with a reducing agent such as hydrogen before use.

Solvents suitable for use in the process of the present invention dissolve or at least partially dissolve the substrate, and completely dissolve the product, but not the catalyst, or its support. The solvent is not susceptible to hydrogenolysis or reductive hydrogenation which could result in the formation of undesirable by-products thus making the recovery of a desired product more complicated. Furthermore a suitable solvent does not adversely affect the activity of the catalyst. Solvents, having a dielectric constant greater than 2 are preferred. The best results in terms of reaction rate and yield of the desired thiol are usually obtained with the most polar solvents. Examples of suitable solvents are tetrahydrofuran, acetonitrile, dichloromethane, ethyl acetate, 1,1-bis(3,4-dimethylphenyl)ethane, o-dichlorobenzene, and their mixtures with water, the benefit of the latter being most apparent in the case of a low polarity solvent. Alternatively the process can be conducted in the absence of a solvent.

The process is typically conducted in a pressure vessel provided with a heater, stirrer or shaker, pressure and temperature measuring devices and inlet/outlet connections to metered gas supply lines. The reactants are not corrosive so that readily available low cost materials, such as mild or stainless steel, can be used for the reactor and auxilliary equipment.

The following ranges of concentrations of the components are given as weight percent based on the total charge to the reactor. The preferred ranges are those which result in the most economical operation of the process relative to the capacity of the reactor and the yield of desired product. The initial charge of substrate, R—$(X)_a$—SCN or R—$(X)_a$—S—S—$(X)_a$—R, to the reactor is from about 5% to about 99.9%, typically 30% to 60%. The catalyst is from about 0.1% to about 5%, and the balance, if any, is solvent which optionally contains up to 80% by weight water. The molar ratio of substrate to catalyst can typically be between 25:1 and 2000:1, based on the Group VIII metal content of the catalyst.

The reactor is typically purged several times at ambient pressure with a non-oxidizing gas, nitrogen being preferred because it is the least expensive. This is followed by purging several times with hydrogen. The reactor is then closed and the contents are heated to the desired temperature between from about 50° C. and about 250° C. while being thoroughly mixed by stirring or shaking. It is preferred that the reactor be agitated with an efficient stirrer at 800–1800 RPM. The hydrogen pressure is then adjusted to the desired level between from about $14 \times 10^5$ and about $70 \times 10^5$ Pa, although a higher pressure may be used up to the safe limit of the reactor. The temperature and pressure are maintained while continuously agitating the reactants until no further consumption of hydrogen occurs.

During this step of the process the reactor is closed and the hydrogen pressure maintained by added hydrogen as it is consumed in the reaction. Alternatively hydrogen is continuously passed through the reactor while maintaining the hydrogen pressure in the reactor at the desired level throughout the hydrogenolysis step. Using hydrogen as a purge during the process is beneficial since it removes undesirable by products that can poison the catalyst, such as HCN from the hydrogenolysis of thiocyanates, thus improving catalyst performance by extending the active life of the catalyst. The process is followed by monitoring the hydrogen consumption or sampling the liquid solution and the process is usually complete in about 1 to about 15 hours depending on the particular substrate, and the temperature and pressure at which the reaction is conducted.

The temperature and pressure are then adjusted to ambient conditions and the reactor is purged several times with a non-oxidizing gas until free from hydrogen. The reactor is then discharged and the catalyst is separated from the solvent and product by filtering, decanting or centrifuging, with filtering usually being preferred because it is the most economical. The solvent then is separated by distillation or extraction. Distillation is usually the easiest and most economical procedure. Organic thiol recovered by either of the foregoing procedures is purified and analyzed by conventional methods.

The process of the present invention is useful to prepare organic thiols. Organic thiols are useful for the preparation of detergents and as intermediates for the synthesis of a variety of organic compounds such as therapeutic products, for example, mercaptoacyl prolines, potent inhibitors of anglotension-converting enzymes which are used as treatment for hypertension and heart disease. Fluorinated thiols are useful, for example, as fire extinguishing substances for oil fires on water surface and as an additive for paper products or for textile finishing.

EXAMPLES

In the following examples, by "conversion" is meant the mole % of $R-(X)_a-SCN$ or $R-(X)_a-S-S-(X)_a-R$ consumed; "selectivity" is defined as moles $R-(X)_a-SH$ produced divided by moles of $R-(X)_a-SCN$ or $R-(X)_a-S-S-(X)_a-R$ consumed ×100%. Yield is the mole % of $R-(X)_a-SH$ recovered based on the starting $R-(X)_a-SCN$ or $R-(X)_a-S-S-(X)_a-R$.

Example 1

Preparation of 2-perfluorohexyl-ethanethiol (I) by hydrogenolysis of 2-perfluorohexyl-ethanethiocyanate (II)

A 400 cc stainless steel shaker bomb provided with a heater, pressure and temperature gauges and inlet/outlet connections to metered gas supply lines was charged with 150 g (0.37 mole) of $(C_6F_{13}CH_2CH_2SCN)$; 200 g tetrahydrofuran, (A.C.S. reagent grade available from J. T. Baker); 2.0 g prereduced catalyst (5 wt % Pd-0.3 wt % Sn on an activated carbon support); and 2.0 g biphenyl, (available from Aldrich) (internal standard for gas chromatographic analysis). The molar ratio substrate/catalyst was 394 based on Pd metal.

The bomb was purged with nitrogen three times to remove any oxygen followed by purging three times with hydrogen. The hydrogen pressure was adjusted to about $14 \times 10^5$ pascals at room temperature and the reactants were brought to 125° C. The hydrogen pressure was increased to $26.7 \times 10^5$ pascals and the bomb was shaken maintaining these conditions until no further consumption of hydrogen occured, which required about twelve hours. When the hydrogenolysis was complete the temperature and pressure were adjusted to ambient conditions and any remaining hydrogen was removed by purging the bomb three times with nitrogen. A sample was removed and G.C. analysis showed 100% conversion of (II) with 98.2% selectivity to produce (I). No disulfide was detected.

The bomb was discharged and the contents were filtered to isolate the catalyst. Tetrahydrofuran was recovered by distillation at atmospheric pressure. The product (I) was purified by vacuum distillation and 128 g were obtained corresponding to a recovered yield of 91%. Analysis by G.C. and proton NMR showed the purity of the product to be 99.9%.

Example 2

Preparation of 2-perfluorohexyl-ethanethiol (I) by hydrogenolysis of 2-perfluorohexyl-ethanethiocyanate This is an example to illustrate the effect of using a Pd catalyst which does not incorporate a modifier metal component. The reaction was carried out using the same materials and quantities as those used in Example 1 except that the prereduced catalyst was 5 wt % Pd (2.0 g) on an activated carbon support. The reactor and process conditions were identical with those described in Example 1. A sample was removed from the reactor on completion of the hydrogenolysis and G.C. analysis showed 73.6% conversion of (II) with only 26.2% selectivity to product (I) and 57.3% selectivity to form disulfide. The Pd catalyst gave considerably less conversion of (II) and much lower selectivity for the production of (I). The formation of a large amount of disulfide would necessitate a separation step to recover a much lower yield of (I) than that obtained in Example 1.

Example 3

Preparation of 2-perfluorohexyl-mercaptoethane(I) by hydrogenolysis of bis-(2-perfluorohexylethane)-disulfide (III)

The procedure described in Example 1 was conducted with the initial charge to the shaker bomb being 70.1 g (0.093 mole) of (III) $(C_6F_{13}CH_2CH_2S-)_2$, 50 g tetrahydrofuran, 0.5 g prereduced catalyst (5 wt % P-0.3 wt % Sn on activated carbon support) and 2.0 g biphenyl. The molar ratio substrate/catalyst was 388.

On completion of the hydrogenolysis a sample taken from the bomb and analyzed by G.C. showed 100% conversion of (III) with 92.8% selectivity to produce (I).

Examples 4–10

The results obtained using different solvents in the process are summarized in Table 1. The reactor and process conditions were identical with those described in Example 1, as were the substrate and the catalyst and the same quantities were added to the reactor as those used in Example 1.

TABLE 1

| | Hydrogenolysis of (I) in Different Solvents | | |
|---|---|---|---|
| | | Conversion | Selectivity |
| Ex. | Solvent | % (I) | % (II) | % (III) |
| 4 | Isopropanol | 99 | 27 | 35 |
| 5 | 1,1-Bis(3,4-dimethyl-phenyl) ethane | 73 | 84 | 0 |
| 6 | o-Dichlorobenzene | 52 | 97 | 3 |
| 7 | Ethyl Acetate | 99 | 93 | 0 |
| 8 | Acetic Acid | 98 | 79 | 0 |
| 9 | Acetonitrile | 100 | 93 | 0 |
| 10 | | 59 | 31 | 75 |

Example 11

Preparation of 2-perfluorohexyl-ethanethiol (I) by hydrogenolysis of 2-perfluorohexyl-ethanethiocyanate (II)

A 400 cc shaker bomb, as described in Example 1, was charged with 75.0 g (0.185 mole) of (II), 100 g dichloromethane, 100 g water, 0.5 g prereduced catalyst (5 wt % Pd-0.3 wt % Sn) on an activated carbon support) and 2.0 g biphenyl (internal standard for G.C. analysis).

The procedure was the same as described in Example 1 except that the reaction was conducted at 150° C. and $26.7 \times 10^5$ pascals for 12 hours. On completion of the reaction a sample analyzed by G.C. showed 100% conversion of (II) with 99% selectivity to produce (I). A small amount (1%) of disulfide was found to be present.

Example 12

Preparation of Telomer B Thiol by hydrogenolysis of Telomer B Thiocyanate

A 400 cc shaker bomb, as described in Example 1 was charged with 54.5 g (0.108 mole) of Telomer B Thiocyanate (Zonyl® TTS, M.W.=505) supplied by E. I. du Pont de Nemours and Co., Wilmington, Del, 72 g dichloromethane, 72 g water, 0.25 g prereduced catalyst (5 wt % Pd-0.5 wt % Sn on an activated carbon support) and 1.0 g biphenyl (internal standard for G.C. analysis).

The procedure was the same as described in Example 11. On completion of the reaction a sample analyzed by G.C. showed 99% conversion of Telomer B Thiocyanate with 99.5% selectivity to produce Telomer B Thiol. A small amount (0.5%) of Telomer B Disulfide was also obtained.

Example 13

Preparation of n-Octyl Thiol(I) by Hydrogenolysis of n-Octyl Thiocyanate (II)

A 400 cc shaker bomb, as described in Example 1, was charged with 20.0 g(0.117 mole) of (II), 180 g tetrahydrofuran, 2.00 g prereduced catalyst (5 wt % Pd-0.5wt % Sn on an activated carbon support), and 1.0 g ortho dichlorobenzene(internal standard for G.C. analysis). The hydrogen pressure was adjusted to $26.7 \times 10^5$ Pa at room temperature and the reactants were brought to 150° C. The hydrogen pressure was increased to $70 \times 10^5$ Pa and reacted for 12 hours. At the end of the reaction a sample analyzed by G.C. showed a 99.6% conversion of (II) to (I)(92% selectivity) and n-octyl disulfide(6% selectivity).

Example 14

Preparation of Benzyl Thiol(I) by Hydrogenolysis of Benzyl Disulfide(II)

A 400 cc shaker bomb, as described in Example 1, was charged with 12.3 g(0.05 mole) of (II), 100 g tetrahydrofuran, 1.0 g prereduced catalyst(5 wt %Pd-0.5 wt % Sn on an activated carbon support), and 1.0 g biphenyl (internal standard for G.C. analysis). The hydrogen pressure was adjusted to $26.7 \times 10^5$ Pa at room temperature and the reactants were brought to 150° C. The hydrogen pressure was increased to $70 \times 10^5$ Pa and reacted for 12 hours. At the end of the reaction a sample analyzed by G.C. showed a 91% conversion of (II) to (I) (87% selectivity) and toluene(17% selectivity).

Example 15

Preparation of 2-perfluorohexyl-ethanethiol(I) by hydrogenolysis of 2-perfluorohexyl-ethanethiocyanate (II)

A one liter Hastelloy autoclave equipped with a stirrer, thermocouple, dip tube, and gas inlet and outlet couplings was charged with 225 g (0.555 mole) of (II), 300 g ethyl acetate, 1.3 g reduced catalyst(5 wt % Pd-0.5 wt % Sn on an activated carbon support), and 3.00 g biphenyl (internal standard for G.C. analysis). The bomb was purged with nitrogen three times to eliminate any oxygen. The autoclave was pressurized to $26.7 \times 10^5$ Pa with hydrogen and the hydrogen feed mass flow controller was adjusted to 0.3 standard liter per minute for a continuous purge of hydrogen through the autoclave while stirring at 1100 RPM. The reaction mixture was heated to 175° C. at $26.7 \times 10^5$ Pa constant pressure. The reaction was run under these conditions for four hours and then cooled to room temperature. The mixture was then pressurized with nitrogen to $6.7 \times 10^5$ Pa and vented several times. The G.C. analysis showed a 100% conversion of (II) to (I) (96% selectivity).

Example 16

Preparation of Telomer B Thiol by hydrogenolysis of Telomer B Thiocyanate

The same one liter autoclave as described in Example 15 was charged with 218 g(0.432 mole) of Telomer B Thiocyanate(Zonyl TTS, M.W=505) supplied by E. I. du Pont de Nemours and Co., Wilmington, Del., 218 g ethyl acetate, 1.0 g prereduced catalyst(5 wt % Pd-0.5 wt % Sn on an activated carbon support), and 3.00g biphenyl(internal standard for G.C. analysis). The reaction mixture was heated to 175° C. at $26.7 \times 10_5$ Pa constant pressure for four hours. The G.C. analysis showed a 100% conversion of Telomer B Thiocyanate to Telomer B Thiol (99% selectivity) and Telomer B Disulfide(1% selectivity).

Example 17

Preparation of Telomer B thiol by hydrogenolysis of Telomer B Thiocyanate

The autoclave and reactants employed were the same as in Example 16, but the reaction mixture was heated at 175° C. at $46.7 \times 10^5$ Pa constant hydrogen pressure for 1.5 hours. The G.C. analysis showed a 100% conversion of Telomer B Thiocyanate to Telomer B Thiol (99% selectivity) and Telomer B Disulfide(1% selectivity).

Example 18

Preparation of Telomer B Thiol by hydrogenolysis of Telomer B Thiocyanate

The autoclave, reactants, and conditions were the same as in Example 17 except the 1.0 g prereduced catalyst(5 wt % Pd-0.5wt % Sn on an activated support) was replaced with 1.0g prereduced 5 wt % Pd on an activated carbon support. The G.C. analysis showed a 91% conversion of Telomer B Thiocyanate to Telomer B Thiol (89% selectivity) and Telomer B Disulfide(10% selectivity).

What is claimed is:

1. A process for the preparation of a thiol of formula I or formula II

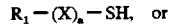  I

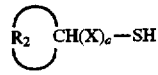  II wherein

X is $(CH_2)_m$ wherein m is 1 or 2;

a is zero or 1;

$R_1$ is:

$C_1$–$C_{30}$ linear, branched, or cyclic alkyl optionally substituted with a $C_1$–$C_{30}$ perfluororalkyl;

$C_1$–$C_{30}$ perfluoroalkyl;

H—D—G or F—E—G wherein

D is —$(CH_2)_b$—;

E is —$(CF_2)_b$—;

G is —[A —$(CH_2)_c]_d$—$(CH_2)_e$—, —[A—$(CF_2)_c]_d$— $(CF_2)_e$—, —[A —$(CF_2)_c]_d$—$(CH_2)_e$—, or —[A— $(CH_2)_c]_d$—$(CF_2)_e$—;

wherein each A is independently selected from the group consisting of —$N(R_3)$—, —$C(O)N(R_3)$—, —$CO_2$—, —$SO_2N(R_3)$—, —O—, and —S—; wherein $R_3$ is H, $C_1$–$C_{30}$ alkyl, or $C_1$–$C_{30}$ perfluroralkyl; each b and e is independently zero or a positive integer of 1 to 29, and each c and d is independently a positive integer of 1 to 30, provided that b+e+(c×d) is less than or equal to 30; and $C_6$–$C_{30}$ aryl optionally substituted with $C_1$–$C_{24}$ alkyl, $C_1$–$C_{24}$ perfluoroalkyl, F, Br, Cl N(R3)2, CON(R3)2, CO2(R3), CO(R3), SO2N(R3)2, O(R3), or S($R_3$) wherein $R_3$ is H, $C_1$–$C_{30}$ alkyl, or $C_1$–$C_{30}$ perfluoroalkyl; and $R_2$ is —D—G— or —E— G—wherein D, E and G are as defined above provided that b+e+(c×d) is less than or equal to 8;

said process comprising reacting hydrogen with

A. a thiocyanate of formula III

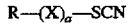   III or

B. a disulfide of formula IV

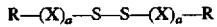   IV wherein R is $R_1$ or $R_2$ as defined above and X and a are as defined above, wherein the reaction with thiocyanate is conducted in the presence of a catalyst comprising a Group VIII metal or a mixture thereof; and the reaction with thiocyanate or with disulfide is conducted in the presence of a catalyst comprising a Group VIII metal or mixture thereof in the presence of a modifier metal selected from a group consisting of Group IB, Group IIB, Group IIIA, Group IVA, Group VA and Group VIA metal or mixture thereof, said catalyst being on a porous insoluble support.

2. The process of claim 1 wherein for the catalyst the Group VIII is selected from the group consisting of Pd, Pt and Ru and the modifier metal is selected from the group consisting of Cu, Ag, Au, Sn, Pb, Bi, In, Tl, S, Se, and Te.

3. The process of claim 2 wherein the support for the catalyst is activated carbon, alumina, silica, silica alumina, zirconia, titania, calcium carbonate, zeolite or magnesia.

4. The process of claim 3 wherein for the catalyst the Group VIII metal is present at from about 1% to 20% by weight and the modifier metal is present at from about 0.1% to about 5% by weight.

5. The process of claim 4 wherein the thiocyanate or disulfide is present from about 5% to about 99.9% by weight and the catalyst is present at from about 0.1% to about 5% by weight.

6. The process of claim 5 conducted at a temperature of from about 50° C. to about 250° C. and a pressure of from about 14×10$^5$ to about 70×10$^5$ Pa with agitation.

7. The process of claim 6 conducted in a solvent having a dielectric constant greater than 2.

8. The process of claim 7 wherein the solvent is ethyl acetate, and the catalyst is prereduced Pd/Sn on activated carbon.

9. The process of claim 8 wherein the thiocyanate is Telomer B thiocyanate, or the disulfide is Telomer B disulfide.

* * * * *